(12) United States Patent
Patil et al.

(10) Patent No.: US 7,977,286 B2
(45) Date of Patent: *Jul. 12, 2011

(54) LUBRICATING COMPOSITIONS CONTAINING ASHLESS CATALYTIC ANTIOXIDANT ADDITIVES

(75) Inventors: Abhimanyu O. Patil, Westfield, NJ (US); Jacob J. Habeeb, Westfield, NJ (US); Michael E. Landis, Mullica Hill, NJ (US); Manuel A. Francisco, Phillipsburg, NJ (US); Manika Varma-Nair, Warren, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 660 days.

This patent is subject to a terminal disclaimer.

(21) Appl. No.: 11/732,326

(22) Filed: Apr. 3, 2007

(65) Prior Publication Data

US 2007/0265178 A1 Nov. 15, 2007

(51) Int. Cl.
*C10M 133/12* (2006.01)
(52) U.S. Cl. ........................ 508/557; 252/401
(58) Field of Classification Search .................. 508/192, 508/557; 252/401
See application file for complete search history.

(56) References Cited

U.S. PATENT DOCUMENTS

| | | | | |
|---|---|---|---|---|
| 2,361,391 A | * | 10/1944 | Maxwell et al. | 508/557 |
| 2,930,758 A | | 3/1960 | Tierney et al. | |
| 3,432,460 A | * | 3/1969 | Spacht | 524/255 |
| 3,498,916 A | * | 3/1970 | Coupland et al. | 508/557 |
| 3,882,032 A | | 5/1975 | Bird et al. | |
| 4,966,721 A | * | 10/1990 | Farng et al. | 508/557 |
| 5,213,699 A | * | 5/1993 | Babiarz et al. | 508/557 |
| 5,831,128 A | | 11/1998 | Beller et al. | |
| 6,521,793 B1 | | 2/2003 | Guram et al. | |
| 6,531,607 B2 | | 3/2003 | Goossen et al. | |
| 2008/0248985 A1 | * | 10/2008 | Patil et al. | 508/557 |
| 2009/0048130 A1 | * | 2/2009 | Habeeb et al. | 508/366 |

FOREIGN PATENT DOCUMENTS

WO    WO 03/006420 A1    1/2003

OTHER PUBLICATIONS

Jean Bourson, "Benzimidazole. I. Synthesis and Oxidation-Reduction of the 1,3-diphenylbenzimidazolium Salts", *Bulletin de la Societe Chimique de France*, 1970, vol. 5, pp. 1867-1872 (Abstract Only).
Mosatomo Norma, "Synthesis of Phenazine and Phenothiazine Derivatives by the Oxidative Cyclization of Hydrazobenzenes and Sulfenamides", *Kenkyu Hokoku—Asahi Garasu Kogyo Gijutsu Shoreikai*, 1978, vol. 32, pp. 51-60 (Abstract Only).
Christopher Chan, et al., "Sulfenamides and Sulfinamindes VI. Reactions of Aryl Sulfenamids with Diphenylpicrylhydrazyl Free Radical", *Phosphorus, Sulfur, and Silicon*, 1991, vol. 55, pp. 261-269.
Tian-Bao Huang, et al., "The Synthesis and Reaction of Heterocyclic Thiophosphoryl Chlorides with AlCl3 or CF3SO3Ag. An Attempt to Obtain .lambda.5.sigma, 3-thiophosphoryl cations", Phosphorus, Sulfur and Silicon and the Related Elements, 2000, vol. 156, pp. 9-20 (Abstract Only).
Manas Chakrabarty, et al., "On Attempted Oxidative Cyclisation of Isomeric N,N'-Diphenylphenylenediamines and Their N,N'-Dimethyl Derivatives by Palladium(II) Acetate and UV Light", *Synthetic Communications*, vol. 30, pp. 3651-3668.
Todd Wenderski, et al., "Pd Catalyed Coupling of 1,2-dibromoarenes and Anilines: Formation of N,N-diaryl-o-phenylenediamines", *Tetrahedron Letters*, 2004, 45(37), pp. 6851-6853.
Wen Huang, et al., "Palladium-benzimidazolium Salt Catalyst Systems for Suzuki Coupling: Development of a Practical and Highly Active Palladium Catalyst System for Coupling of Aromatic Halides with Arylboronic Acids", *Tetrahedron Letters*, 2005, 61(41), pp. 9783-9790.
Hidehiro Sakurai, et al., "Synthesis and Oxidation of (benzimidazolylidene)Cr(CO)5 Complexes", *Journal of Organometallic Chemistry*, 2005, 690(7), pp. 1750-1755.

* cited by examiner

*Primary Examiner* — Ellen M McAvoy
*Assistant Examiner* — Ming Cheung Po
(74) *Attorney, Agent, or Firm* — Liza Montalvo; Robert Migliorini

(57) ABSTRACT

The invention comprises lubricating compositions and hydraulic fluids containing N,N'-diaryl-o-phenylenediamine compounds that impart good levels of oxidation inhibition in the lubricants and hydraulic fluids. The invention further comprises a method of making N,N'-diaryl-o-phenylenediamine compounds.

12 Claims, No Drawings

LUBRICATING COMPOSITIONS CONTAINING ASHLESS CATALYTIC ANTIOXIDANT ADDITIVES

FIELD OF THE INVENTION

The present invention relates to lubricant compositions including passenger car engine oils, commercial vehicle engine oils, industrial, marine, hydraulic, aviation, and driveline oils containing ashless catalytic antioxidant additives and to a method of making said additives.

BACKGROUND OF THE INVENTION

A wide variety of additives are used in lubricating oils, greases and hydraulic fluids to improve their properties and enhance their performance. Additives can improve the performance of lubricating oils, greases and hydraulic fluids with respect to oxidation, wear and corrosion. One important property is oxidative stability. Antioxidants slow oxidative degradation by retarding or inhibiting a variety of degradation chemistries, thereby protecting and extending the life of formulated oils. Antioxidancy is described as the ability of an additive to delay the onset of oxidation by effectively quenching radicals that are generated by a system.

Many conventional antioxidants are stoichiometrically consumed in the degradation process. That is, conventional antioxidants are consumed in neutralizing a variety of degradation chemistries. More effective antioxidants are catalytic antioxidants. Catalytic antioxidants extend the useful life of formulated lubricants and may be used in significantly reduced concentration while maintaining good performance levels.

It would be desirable, therefore, to provide lubricating compositions and hydraulic fluids with antioxidants that perform more like catalysts in their antioxidation function, thereby enhancing the performance and extending the life of such lubricants and fluids.

Furthermore, it would be of great industrial interest to develop a process in which antioxidants that perform more like catalysts in their antioxidation function could be prepared from generally available starting compounds that are relatively inexpensive, available in commercial scale amounts and that are safe to handle.

SUMMARY OF THE INVENTION

It has now been discovered that substituted N,N'-diaryl-o-phenylenediamine compounds impart good levels of oxidation inhibition in lubricants and hydraulic fluids to which the compounds have been added.

Thus, in one embodiment, there is provided a composition comprising a major amount of lubricant or hydraulic fluid and an effective amount of at least one substituted N,N'-diaryl-o-phenylenediamine antioxidant.

In another embodiment, there is provided a method of making substituted N,N'-diaryl-o-phenylenediamine antioxidants of the invention.

In still another embodiment, there is provided a method for improving the oxidative stability of compositions comprising lubricants or hydraulic fluids using the substituted N,N'-diaryl-o-phenylenediamine antioxidants of the present invention.

Other objects and advantages of the present invention will become apparent from the detailed description that follows.

The antioxidants used in this composition include those having the Formula I

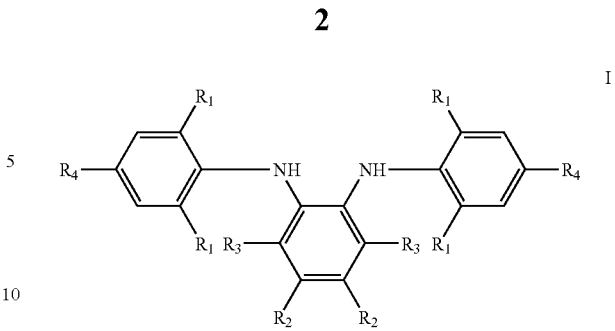

where $R_1$ is H or $C_1$ to $C_{12}$ alkyl, $R_2$ is H or $C_1$ to $C_{12}$ alkyl, and $R_3$ and $R_4$ are independently H or $C_1$ to $C_{12}$ alkyl.

DETAILED DESCRIPTION OF THE INVENTION

The present invention relates to compositions comprising a major amount of lubricant or hydraulic fluid and an effective amount of at least one substituted N,N'-diaryl-o-phenylenediamine antioxidant. These compositions exhibit good levels of oxidative stability.

The compositions of the invention comprise a major amount of lubricant or hydraulic fluid, in particular those lubricants or hydraulic fluids based on paraffinic and naphthenic oils or synthetic oils. Thus, the lubricant can be oil or grease based on a mineral oil or a synthetic oil.

Typical paraffinic and naphthenic oils include conventional mineral oils or hydrotreated oil. Other useful fluids of lubricating viscosity include non-conventional base stocks that have been processed, preferably catalytically, or synthesized to provide high performance lubrication characteristics.

Formulated lubricant compositions comprise a mixture of a base stock or a base oil and at least one performance additive. Usually, the base stock is a single oil secured from a single crude source and subjected to a single processing scheme and meeting a particular specification. Base oils comprise at least one base stock.

Non-conventional or unconventional base oils include one or more of a mixture of base stock(s) derived from one or more Gas-to-Liquids (GTL) materials, as well as hydrodewaxed, or hydroisomerized/conventional catalytically (or solvent) dewaxed base stock(s) derived from natural wax or waxy feeds, mineral and or non-mineral oil waxy feed stocks such as slack waxes, natural waxes, and waxy stocks such as gas oils, waxy fuels hydrocracker bottoms, waxy raffinate, hydrocrackate, thermal crackates, or other mineral, mineral oil, or even non-petroleum oil derived waxy materials such as waxy materials received from coal liquefaction or shale oil, and mixtures of such base stocks.

GTL base oils comprise base stock(s) obtained from GTL materials that are derived via one or more synthesis, combination, transformation, rearrangement, and/or degradation/deconstructive processes from gaseous carbon containing compounds. Preferably, the GTL base stocks are derived from the Fischer-Trospch (FT) synthesis process wherein a synthesis gas comprising a mixture of $H_2$ and CO is catalytically converted to lower boiling materials by hydroisomerisation and/or dewaxing. The process is described, for example, in U.S. Pat. Nos. 5,348,982 and 5,545,674, and examples of suitable catalysts are described in U.S. Pat. No. 4,568,663, each of which is incorporated herein by reference.

GTL base stock(s) are characterized typically as having kinematic viscosities at 100° C. of from about 2 mm²/s to about 50 mm²/s, preferably from about 3 mm²/s to about 50 mm²/s, more preferably from about 3.5 mm²/s to about 30 mm²/s. The GTL base stock and/or other hydrodewaxed, or hydroisomerized/catalytically (or solvent) dewaxed wax derived base stock(s) used in the present invention have kinematic viscosities at 100° C. in the range of about 3.5 mm²/s to 7 mm²/s, preferably about 4 mm²/s to about 7 mm²/s, more preferably about 4.5 mm²/s to 6.5 mm²/s. Reference herein to kinematic viscosity refers to a measurement made by ASTM method D445.

GTL base stocks and base oils derived from GTL base stocks which can be used as base stock components of this invention are further characterized typically as having pour points of about −5° C. or lower, preferably about −10° C. or lower, more preferably about −15° C. or lower, still more preferably about −20° C. or lower, and under some conditions may have advantageous pour points of about −25° C. or lower, with useful pour points of about −30° C. to about −40° C. or lower. In the present invention, however, the GTL base stock(s) used generally are those having pour points of about −30° C. or higher, preferably about −25° C. or higher, more preferably about −20° C. or higher. References herein to pour point refer to measurement made by ASTM D97 and similar automated versions.

The GTL base stock(s) derived from GTL materials, especially hydro-dewaxed or hydroisomerized/catalytically (or solvent) dewaxed F-T material derived base stock(s), and other such wax-derived base stock(s) which are base stock components which can be used in this invention are also characterized typically as having viscosity indices of 80 or greater, preferably 100 or greater, and more preferably 120 or greater. Additionally, in certain particular instances, the viscosity index of these base stocks may be preferably 130 or greater, more preferably 135 or greater, and even more preferably 140 or greater. For example, GTL base stock(s) that derive from GTL materials preferably F-T materials especially F-T wax generally have a viscosity index of 130 or greater. References herein to viscosity index refer to ASTM method D2270.

In addition, the GTL base stock(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stocks and base oils typically have very low sulfur and nitrogen content, generally containing less than about 10 ppm, and more typically less than about 5 ppm of each of these elements. The sulfur and nitrogen content of GTL base stock and base oil obtained by the hydroisomerization/isodewaxing of F-T material, especially F-T wax is essentially nil.

In a preferred embodiment, the GTL base stock(s) comprises paraffinic materials that consist predominantly of non-cyclic isoparaffins and only minor amounts of cycloparaffins. These GTL base stock(s) typically comprise paraffinic materials that consist of greater than 60 wt % non-cyclic isoparaffins, preferably greater than 80 wt % non-cyclic isoparaffins, more preferably greater than 85 wt % non-cyclic isoparaffins, and most preferably greater than 90 wt % non-cyclic isoparaffins.

Examples of useful compositions of GTL base stock(s) are recited in U.S. Pat. Nos. 6,080,301; 6,090,989, and 6,165,949 for example, which are herein incorporated by reference.

Base stock(s), derived from waxy feeds, which are also suitable for use in this invention, are paraffinic fluids of lubricating viscosity derived from hydrodewaxed, or hydroisomerized/catalytically (or solvent) dewaxed waxy feedstocks of mineral oil, non-mineral oil, non-petroleum, or natural source origin, e.g., feedstocks such as one or more of gas oils, slack wax, waxy fuels hydrocracker bottoms, hydrocarbon raffinates, natural waxes, hyrocrackates, thermal crackates, foots oil, wax from coal liquefaction or from shale oil, or other suitable mineral oil, non-mineral oil, non-petroleum, or natural source derived waxy materials, linear or branched hydrocarbyl compounds with carbon number of about 20 or greater, preferably about 30 or greater, and mixtures of such isomerate/isodewaxate base stocks and base oils.

Slack wax is the wax recovered from any waxy hydrocarbon oil including synthetic oil such as F-T waxy oil or petroleum oils by solvent or autorefrigerative dewaxing. Solvent dewaxing employs chilled solvent such as methyl ethyl ketone (MEK), methyl isobutyl ketone (MIBK), mixtures of MEK/MIBK, mixtures of MEK and toluene, while autorefrigerative dewaxing employs pressurized, liquefied low boiling hydrocarbons such as propane or butane.

Slack wax(es) secured from synthetic waxy oils such as F-T waxy oil will usually have zero or nil sulfur and/or nitrogen containing compound content. Slack wax(es) secured from petroleum oils, may contain sulfur and nitrogen containing compounds. Such heteroatom compounds must be removed by hydrotreating (and not hydrocracking), as for example by hydrodesulfurization (HDS) and hydrodenitrogenation (HDN) so as to avoid subsequent poisoning/deactivation of the hydroisomerization catalyst.

The preferred base stocks or base oils derived from GTL materials and/or from waxy feeds are characterized as having predominantly paraffinic compositions and are further characterized as having high saturates levels, low-to-nil sulfur, low-to-nil nitrogen, low-to-nil aromatics, and are essentially water-white in color.

A preferred GTL liquid hydrocarbon composition is one comprising paraffinic hydrocarbon components in which the extent of branching, as measured by the percentage of methyl hydrogens (BI), and the proximity of branching, as measured by the percentage of recurring methylene carbons which are four or more carbons removed from an end group or branch ($CH_2 \geq 4$), are such that: (a) BI−0.5($CH_2 \geq 4$)>15; and (b) BI+0.85 ($CH_2 \geq 4$)<45 as over said liquid hydrocarbon composition as a whole.

The preferred GTL base oil can be further characterized, if necessary, as having less than 0.1 wt % aromatic hydrocarbons, less than 20 wppm nitrogen containing compounds, less than 20 wppm sulfur containing compounds, a pour point of less than −18° C., preferably less than −30° C., a preferred BI≧25.4 and ($CH_2 \geq 4$)≦22.5. They have a nominal boiling point of 370° C.$^+$, on average they average fewer than 10 hexyl or longer branches per 100 carbon atoms and on average have more than 16 methyl branches per 100 carbon atoms. They also can be characterized by a combination of dynamic viscosity, as measured by CCS at −40° C., and kinematic viscosity, as measured at 100° C. represented by the formula: DV (at −40° C.) <2900 (KV at 100° C.) −7000.

The preferred GTL base oil is also characterized as comprising a mixture of branched paraffins characterized in that the lubricant base oil contains at least 90% of a mixture of branched paraffins, wherein said branched paraffins are paraffins having a carbon chain length of about $C_{20}$ to about $C_{40}$, a molecular weight of about 280 to about 562, a boiling range of about 650° F. to about 1050° F., and wherein said branched paraffins contain up to four alkyl branches and wherein the free carbon index of said branched paraffins is at least about 3.

GTL base oils, and hydrodewaxed, or hydroisomerized/catalytically (or solvent) dewaxed wax base oils, for example, hydroisomerized or hydrodewaxed waxy synthesized hydrocarbon, e.g., Fischer-Tropsch waxy hydrocarbon base oils are of low or zero sulfur and phosphorus content. There is a movement among original equipment manufacturers and oil formulators to produce formulated oils of ever increasingly reduced sulfated ash, phosphorus and sulfur content to meet ever increasingly restrictive environmental regulations. Such oils, known as low SAPS oils, would rely on the use of base oils which themselves, inherently, are of low or zero initial sulfur and phosphorus content. Such oils when used as base oils can be formulated with additives. Even if the additive or additives included in the formulation contain sulfur and/or phosphorus the resulting formulated lubricating oils will be lower or low SAPS oils as compared to lubricating oils formulated using conventional mineral oil base stocks.

Low SAPS formulated oils for vehicle engines (both spark ignited and compression ignited) will have a sulfur content of 0.7 wt % or less, preferably 0.6 wt % or less, more preferably 0.5 wt % or less, most preferably 0.4 wt % or less, an ash content of 1.2 wt % or less, preferably 0.8 wt % or less, more preferably 0.4 wt % or less, and a phosphorus content of 0.18% or less, preferably 0.1 wt % or less, more preferably 0.09 wt % or less, most preferably 0.08 wt % or less, and in certain instances, even preferably 0.05 wt % or less.

While the preferred base oils used according to this invention are GTL base oils, other synthetic oils may be used. Other synthetic oils that can be used in the invention include polyalphaolefins (PAOs), aliphatic or aromatic carboxylic esters, phosphoric acid esters, and the like. The PAOs, which are known materials and generally available on a major commercial scale from suppliers such as ExxonMobil Chemical Company, Chevron, BP-Amoco, and others, typically vary in number average molecular weight from about 250 to about 3000, or higher. PAOs are commercially available in wide range of kinematic viscosities, such as, up to about 100 cSt (kV at 100° C.) and up to about 3000 cSt (kV at 100° C.), or higher. The PAOs are typically comprised of hydrogenated polymers or oligomers of alphaolefins which include, but are not limited to, about $C_2$ to about $C_{32}$ alphaolefins with about $C_8$ to about $C_{16}$ alphaolefins, such as 1-octene, 1-decene, 1-dodecene and the like, being is preferred. The preferred polyalphaolefins are poly-1-octene, poly-1-decene and poly-1-dodecene and mixtures thereof and mixed olefin-derived polyolefins. The dimers of higher olefins in the range of about $C_8$ to $C_{20}$, preferably $C_{14}$ to $C_{18}$, may be used to provide low viscosity base stocks of acceptably low volatility. Depending on the viscosity grade and the starting oligomer, the PAOs may be predominantly trimers and tetramers of the starting olefins, with minor amounts of the higher oligomers. Most commonly, PAOs having a kinematic viscosity at 100° C. ranging from about 1.5 to 12 cSt are used.

PAO base oils may be conveniently made by the polymerization of an alphaolefin in the presence of a polymerization catalyst such as the Friedel-Crafts catalysts including, for example, aluminum trichloride, boron trifluoride or complexes of boron trifluoride with water, alcohols such as ethanol, propanol or butanol, carboxylic acids or esters such as ethyl acetate or ethyl propionate. For example the methods disclosed by U.S. Pat. Nos. 4,149,178 or 3,382,291 may be conveniently used herein. Other descriptions of PAO synthesis are found in the following U.S. Pat. Nos. 3,742,082; 3,769,363; 3,876,720; 4,239,930; 4,367,352; 4,413,156; 4,434,408; 4,910,355; 4,956,122; and 5,068,487. The dimers of the $C_{14}$ to $C_{18}$ olefins are described in U.S. Pat. No. 4,218,330.

Other useful synthetic lubricating base stock oils such as silicon-based oil or esters of phosphorus containing acids may also be utilized. Examples of other synthetic lubricating base stocks are disclosed in "Synthetic Lubricants", Gunderson and Hart, Reinhold Publ. Corp., NY 1962, which is incorporated in its entirety.

Other suitable synthetic base oils include alkylated aromatic base oils, such as mono- or poly-alkylbenzenes or mono- or poly-alkyl naphthalenes. In is these types of base oils, alkyl substituents are typically alkyl groups of about 8 to 25 carbon atoms, usually from about 10 to 18 carbon atoms and up to about three such substituents may be present, as described for the alkylbenzenes in ACS Petroleum Chemistry Preprint 1053-1058, "Poly n-Alkylbenzene Compounds: A Class of Thermally Stable and Wide Liquid Range Fluids", Eapen et al, Phila. 1984. Tri-alkylbenzenes may be produced by the cyclodimerization of 1-alkynes of 8 to 12 carbon atoms as described in U.S. Pat. No. 5,055,626. Other alkylbenzenes are described in European Patent Application 168 534 and U.S. Pat. No. 4,658,072. Alkylbenzenes are used as lubricant base stocks and base oils, especially for low-temperature applications (arctic vehicle service and refrigeration oils) and in papermaking oils. They are commercially available from producers of linear alkylbenzenes (LABs) such as Vista Chem. Co., Huntsman Chemical Co., Chevron Chemical Co., and Nippon Oil Co. Linear alkylbenzenes typically have good low pour points and low temperature viscosities and VI values greater than about 100, together with good solvency for additives. Other alkylated aromatics which may be used when desirable are described, for example, in "Synthetic Lubricants and High Performance Functional Fluids", Dressler, H., chap 5, (R. L. Shubkin (Ed.)), Marcel Dekker, NY, 1993.

Alkylene oxide polymers and interpolymers and their derivatives containing modified terminal hydroxyl groups obtained by, for example, esterification or etherification are useful synthetic lubricating oils. By way of example, these oils may be obtained by polymerization of ethylene oxide or propylene oxide, the alkyl and aryl ethers of these polyoxyalkylene polymers (methyl-polyisopropylene glycol ether having an average molecular weight of about 1000, diphenyl ether of polyethylene glycol having a molecular weight of about 500-1000, and the diethyl ether of polypropylene glycol having a molecular weight of about 1000 to 1500, for example) or mono- and poly-carboxylic esters thereof (the acidic acid esters, mixed $C_{3-8}$ fatty acid esters, or the $C_{13}$Oxo acid diester of tetraethylene glycol, for example).

Esters comprise a useful base stock. Additive solvency and seal compatibility characteristics may be secured by the use of esters such as the esters of dibasic acids with monoalkanols and the polyol esters of mono-carboxylic acids. Esters of the former type include, for example, the esters of dicarboxylic acids such as phthalic acid, succinic acid, alkyl succinic acid, alkenyl succinic acid, maleic acid, azelaic acid, suberic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those full or partial esters which are obtained by reacting one or more polyhydric alcohols (preferably the hindered polyols such as the neopentyl polyols, e.g., neopentyl glycol, trimethylol ethane, 2-methyl-2-propyl-1,3-propanediol, trimethylol propane, pentaerythritol and dipentaerythritol) with alkanoic acids containing at least about 4 carbon atoms (preferably $C_5$ to $C_{30}$ acids such as saturated straight chain fatty acids including caprylic acid, capric acid, lauric acid, myristic acid, palmitic acid, stearic acid, arachic acid, and behenic acid, or the corresponding branched chain fatty acids or unsaturated fatty acids such as oleic acid).

Suitable synthetic ester components include the esters of trimethylol propane, trimethylol butane, trimethylol ethane, pentaerythritol and/or dipentaerythritol with one or more monocarboxylic acids containing from about 5 to about 10 carbon atoms.

Silicon-based oils are another class of useful synthetic lubricating oils. These oils include polyalkyl-, polyaryl-, polyalkoxy-, and polyaryloxy-siloxane oils and silicate oils. Examples of suitable silicon-based oils include tetraethyl silicate, tetraisopropyl silicate, tetra-(2-ethylhexyl)silicate, tetra-(4-methylhexyl)silicate, tetra-(p-tert-butylphenyl)silicate, hexyl-(4-methyl-2-pentoxy)disiloxane, poly(methyl)siloxanes, and poly-(methyl-2-mehtylphenyl)siloxanes.

Another class of synthetic lubricating oil is esters of phosphorous-containing acids. These include, for example, tricresyl phosphate, trioctyl phosphate, diethyl ester of decanephosphonic acid.

Another class of oils includes polymeric tetrahydrofurans, their derivatives, and the like.

The compositions of the invention comprise a major amount of a lubricant or hydraulic fluid and an effective amount of at least one substituted N,N'-diaryl-o-phenylenediamine antioxidant. By a major amount of a lubricant or hydraulic fluid, it is meant that the lubricant or hydraulic fluid is present in an amount ranging from about 50 wt. % to about 99 wt. %, e.g., from about 85 wt. % to about 95 wt. %, based on the total weight of the composition. By an effective amount of at least one substituted N,N'-diaryl-o-phenylenediamine antioxidant, it is meant that the antioxidant is present in amounts ranging from about 0.001 to about 5 wt %, and preferably from about 0.01 to about 1 wt % based on the total weight of composition. The antioxidant may be used alone or in combination with other additives.

The antioxidants used according to the invention are N,N'-diaryl-o-phenylenediamines, preferably those N,N'-diaryl-o-phenylenediamines having the Formula I

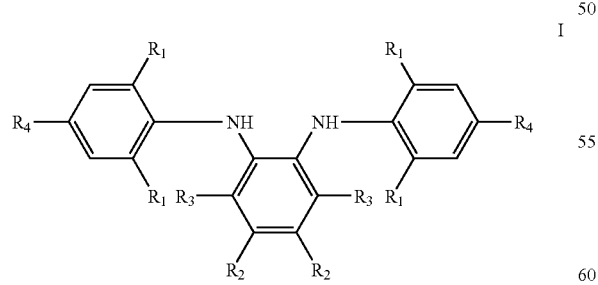

I where $R_1$ is H or $C_1$ to $C_{12}$ alkyl, $R_2$ is H or $C_1$ to $C_{12}$ alkyl, and $R_3$ and $R_4$ are independently H or $C_1$ to $C_{12}$ alkyl. The average molecular weight of the substituted N,N'-diaryl-o-phenylenediamine antioxidant will range from about 200 to about 600, preferably from about 300 to about 500.

Suitable compounds of Formula I include

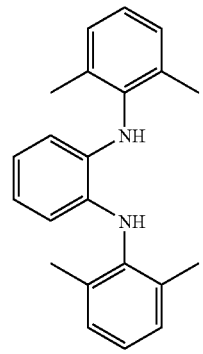

1B

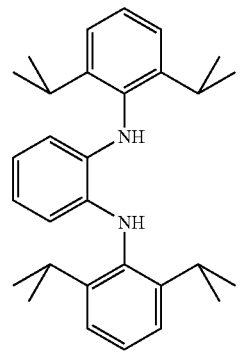

1C

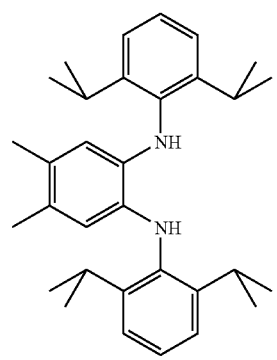

2C

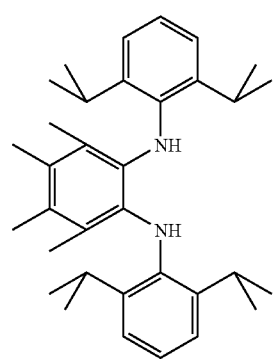

3C

Preferably, $R_1$ is $C_1$ to $C_{10}$ alkyl, most preferably, an alkyl selected from methyl, ethyl, n-propyl, iso-propyl, n-butyl, iso-butyl, tert-butyl and octyl, conveniently a methyl or iso-propyl.

In a separate preferred embodiment, $R_1$ is a methyl and $R_2$, $R_3$ and $R_4$ are independently H or methyl.

Particularly preferred antioxidants are those represented by Structure 1B, 1C, and 2C with that represented by Structure 1B, 1,2-Benzenediamine, N,N'-bis(2,6-dimethylphenyl), as being most preferred.

Unsubstituted N,N'-diaryl-o-phenylenediamines, preferably N,N'-diphenyl-o-phenylenediamine (compound of Formula I, where $R_1=R_2=R_3=R_4=H$), are also an effective antioxidant.

Preferably, the substituted N,N'-diaryl-o-phenylenediamine antioxidant is an isopropyl substituted N,N'-diaryl-o-phenylenediamine antioxidant, more preferably a t-butyl substituted N,N'-diaryl-o-phenylenediamine antioxidant, still more preferably a methyl substituted N,N'-diaryl-o-phenylenediamine antioxidant. Without being bound to any particular theory, it is believed that steric hindrance plays an important role in the antioxidants ability to combat oxidative properties in oils. While some steric hindrance allows for a proton to be donated to an oxidative radical, too much steric hindrance crowds the proton making it unavailable to radicals.

The present invention also relates to methods for preparing the N,N'-diaryl-o-phenylenediamines of the invention. In the prior art, N,N'-diaryl-o-phenylenediamines were prepared by reacting 1,2-dibromoarenes with aniline derivatives using palladium/phosphine or palladium/carbene catalysts as described in Wenderski, T.; Light, K. M.; Orgin, D.; Bott, S. G.; Harlan, C. J. *Tetra. Lett.,* 2004, 45, 6851-6853. In the present invention, substituted N,N'-diaryl-o-phenylenediamine antioxidants are prepared by reacting dibromoarenes or dichloroarenes having Formula II

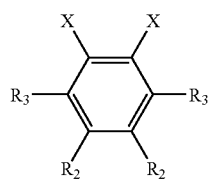

II where X is a halogen, preferably chlorine or bromine, and $R_2$ and $R_3$ have the same meaning as in Formula I, with aniline derivatives having Formula III

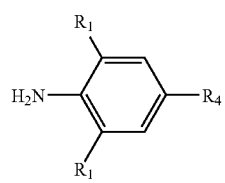

III where $R_1$ and $R_4$ independently are H or $C_1$ to $C_4$ alkyl, in the presence of a palladium catalyst. When X in Formula II is bromine, the palladium catalyst is a preformed palladium complex coupling catalyst.

Substituted N,N'-diaryl-o-phenylenediamine antioxidants can also be prepared by reacting chloro-m-dialkylarenes or bromo-m-dialkylarenes having Formula IV

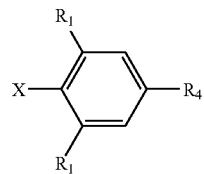

IV where X is a halogen, preferably chlorine or bromine and $R_4$ has the same meaning as in Formula I, with aniline derivatives having Formula V

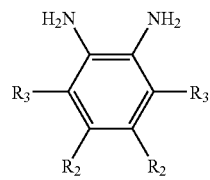

V where $R_2$ and $R_3$ have the same meaning as in Formula I, in the presence of a palladium catalyst.

Both preparation routes described above are carried out in the presence of a palladium catalyst. The palladium catalyst can be a palladium/phosphine or palladium/carbene catalyst. Preferably, the palladium catalyst is a preformed palladium complex coupling catalyst. Aromatic triflates may also be used in is place of the dichloroarenes or chloro-m-dialkylarenes.

Useful aniline derivatives include, but are not limited to, 2-methylaniline; 4-methylaniline; 2,4-dimethylaniline; 2,6-dimethylaniline; 2,4,6-trimethylaniline; 2-ethylaniline; 4-ethylaniline; 2,4-diethylaniline; 2,6-diethylaniline; 2,4-diisopropylaniline; 2,6-diisopropylaniline; 2,4-di-tert-butylaniline; and, 2,6-di-tert-butylaniline.

By preformed palladium complex coupling catalyst, it is meant that the catalyst contains both a palladium and phosphine ligand. The preformed catalysts of the present invention are thermally stable and, in some cases, are air stable making them easier to handle unlike the catalyst system of the prior art which uses tri-t-butylphosphine, a known pyrophoric reagent.

Suitable dibromoarenes of Formula II include, but are not limited to, dibromobenzenes, preferably 1,2 dibromobenzenes. Suitable dichloroarenes of Formula II include, but are not limited to, dichlorobenzenes, preferably 1,2 dichlorobenzenes. Suitable chloro-m-dialkylarenes of Formula IV include, but are not limited to, 2-chloro-m-xylene, 2,6-diethylphenyl chloride, 1-chloro-2,6-diisopropylbenzene, 1-chloro-2,6-di-tert-butylbenzene and 1,3,5-trimethyl-2-chlorobenzene. Suitable bromo-m-dialkylarenes of Formula IV include, but are not limited to, 1-Bromo-2,6-dimethylbenzene (2-bromo-m-xylene), 2,6-diethylphenylbromide, 1-bromo-2,6-diisopropylbenzene, 1-bromo-2,6-di-tert-butylbenzene and 2,4,6-trimethylphenyl bromide.

Preformed palladium complex coupling catalysts of the invention include dichlorobis(triphenylphosphine)palladium (II), tetrakis(triphenylphosphine)palladium(0), diacetato[1,3-bis(diphenylphosphino)propane]palladium(II), dichloro[1,2-bis(diphenylphosphino)ethane]palladium(II), diacetatobis(triphenylphosphine)palladium(II), dichloro[1,4-bis(diphenylphosphino)butane]palladium(II), dichloro[1,1'-bis(diphenylphosphino)ferrocene]palladium(II)-dichloromethane adduct, dichloro[1,1'-bis(diphenylphosphino)

ferrocene]palladium(II)-acetone adduct, di-μ-chlorobis(tris(2,4-di-tert-butylphenyl)phosphite-2-C,P)dipalladium(II), di-μ-bromobis(tri-tert-butylphosphine)dipalladium(I), dichlorobis(tricyclohexylphosphine)palladium(II), dichlorobis(tri-ortho-tolylphosphine)palladium(II), bis(tri-tert-butylphosphine)palladium(0), dichloro[bis(diphenylphosphinophenyl)ether]palladium(II), dichloro[1,1'-bis(di-tert-butylphosphino)ferrocene]palladium(II), dichloro[1,1'-bis(di-isopropylphosphino)ferrocene]palladium(II), dibromobis(tri-ortho-tolylphosphine)palladium(II), dibromo[1,1'-bis(diphenylphosphino)ferrocene]palladium(II), dichlorobis(di-tert-butylphenylphosphine)palladium(II), dichloro(2,2'-bis(diphenylphosphino)-1,1'-binaphthyl)palladium(II), dibromo(2,2'-bis(diphenylphosphino)-1,1'-binaphthyl)palladium(II), diiodo(2,2'-bis(diphenylphosphino)-1,1'-binaphthyl)palladium(II), dichloro[1,3-bis(diphenylphosphino)propane]palladium(II), Fiber supported Pd/P Bu3 catalyst, 1,2,3,4,5-pentaphenyl-1'-(di-tert-butylphosphino)ferrocene, dichlorobis(benzonitrile)palladium(II), dichlorobis(acetonitrile)palladium(II), bis(acetylacetonato)palladium(II), dichloro(1,5-cyclooctadiene)palladium(II), dichloro(norbornadiene)palladium(II), bis(dibenzylideneacetone)palladium(0), tris(dibenzylideneacetone)dipalladium(0), tris(dibenzylideneacetone)dipalladium(0) chloroform adduct, allylpalladium chloride dimmer and palladium(II)acetate trimer.

More preferred preformed palladium complex coupling catalysts of the invention include diacetato[1,3-bis(diphenylphosphino)propane]palladium(II), dichloro[1,2-bis(diphenylphosphino)ethane]palladium(II), diacetatobis(triphenylphosphine)palladium(II), dichloro[1,4-bis(diphenylphosphino)butane]palladium(II), dichloro[1,1'-bis(diphenylphosphino)ferrocene]palladium(II)-dichloromethane adduct, dichloro[1,1'-bis(diphenylphosphino)ferrocene]palladium(II)-acetone adduct, di-μ-chlorobis(tris(2,4-di-tert-butylphenyl)phosphite-2-C,P)dipalladium(I), di-μ-bromobis(tri-tert-butylphosphine)dipalladium(I), dichlorobis(tricyclohexylphosphine)palladium(II), bis(tri-tert-butylphosphine)palladium(0), dichloro[bis(diphenylphosphinophenyl)ether]palladium(II), dichloro[1,1'-bis(di-tert-butylphosphino)ferrocene]palladium(II), dichloro[1,1'-bis(di-isopropylphosphino)ferrocene]palladium(II), dibromobis(tri-ortho-tolylphosphine)palladium(II), dibromo[1,1'-bis(diphenylphosphino)ferrocene]palladium(II), dichlorobis(di-tert-butylphenylphosphine)palladium(II), dichloro(2,2'-bis(diphenylphosphino)-1,1'-binaphthyl)palladium(II), dibromo(2,2'-bis(diphenylphosphino)-1,1'-binaphthyl)palladium(II), diiodo(2,2'-bis(diphenylphosphino)-1,1'-binaphthyl)palladium(II), dichloro[1,3-bis(diphenylphosphino)propane]palladium(II), Fiber supported Pd/P Bu3 catalyst and 1,2,3,4,5-pentaphenyl-1'-(di-tert-butylphosphino)ferrocene. The preformed palladium complex coupling catalysts are commercially available from Johnson Matthey.

The synthesis of N,N'-diaryl-o-phenylenediamines is done under conditions well known to those skilled in the art. In a typical procedure, the reactants are mixed under inert atmosphere (e.g., nitrogen, argon) in a solvent (e.g., toluene) and heated to the boiling temperature of the solvent (e.g., 100-120° C.) under reflux, for a period of about 5 to 24 hours.

Antioxidative properties of the lubricant or hydraulic fluid compositions of the invention are improved by adding an effective amount of at least one substituted N,N'-diaryl-o-phenylenediamine antioxidant to the compositions.

Fully formulated compositions can contain at least one additional lubricating oil or hydraulic fluid additive, which include, but not limited to, viscosity and viscosity index improvers such as polyalkylene or polyolefin viscosity index improvers, metal deactivators such as triazoles and thiadiazoles, extreme pressure and antiwear additives such as phosphate ester, amine phosphate and sulfurized olefins, antirust agents such as carboxylic acids, dispersants such as succinimides, antifoamants and dyes to mention a few. The amount of such other additives included in the formulation will be the amount typically used in formulated oils.

Typical end use applications for the compositions of the invention include, but are not limited to, circulating oils, hydraulic fluids, greases, gear oils, metal working fluids, engine oils and automatic transmission fluids.

The invention is further described by reference to the following comparative examples and non-limiting examples.

EXAMPLES

In the examples and comparative examples, 1 through 22, a series of oils were formulated using as the unadditized base oil one of a polyalphaolefin (PAO) having a kV at 40° C. of 268 cSt, a paraffinic oil derived from a gas to liquid conversion process (GTL) having a kV at 40° C. of 4.0 cSt, a commercially available synthetic motor oil, and a 150N mineral oil.

The antioxidant used in the formulated oils was one of:

L57—a commercially available alkylated diphenyl amine sold by Ciba under the trade name Irganox L57.

1B—1,2-benzenediamine, N,N'-bis(2,6 dimethyl phenyl).

1C—1,2-benzenediamine, N,N'-bis[2,6-bis(1-methyl ethyl)phenyl].

2C—1,2-benzenediamine, N,N'-bis[2,6-bis(1-methyl ethyl)phenyl]-4,5 dimethyl.

3C—1,2-benzenediamine, N,N'-bis[2,6-bis(1-methyl ethyl)phenyl]-3,4,5,6 tetramethyl.

3D—N,N'-bis(2,6-dimethylphenyl)-4,5-dimethyl-o-phenylenediamine

1E—N,N'-bisphenyl-o-phenylenediamine

Comparative Examples 1 and 2 and Examples 1 to 4

In the following runs the data was collected using a DuPont DSC Model 2920 pressure differential scanning calorimeter. The base oil was PAO base oil. The results reported in Table 1 are for isothermal oxidation runs carried out in air (100 psig) at 180° C. using open aluminum pans and 6.5 mg of sample. The samples were heated from room temperature to 180° C. at 10° C./min and then held isothermally to monitor the time taken for the oxidation exotherm to occur. The oxidation induction time (OIT) for each run is shown in Table 1. OIT is calculated as the extrapolation tangent to the exotherm from a plot of heat flow versus time. The OIT is defined as the amount of time taken for the depletion of the antioxidant. In other words, the OIT is the amount of time before oxidation of the lubricant or hydraulic fluid occurs.

TABLE 1

| | Additive, wt % | Oxidation Induction Time, Minutes |
| --- | --- | --- |
| Comp. 1 | None | 2.7 |
| Comp. 2 | L57, 0.5 wt % | 19.4 |
| Example 1 | 1B, 0.5 wt % | 126.8 |
| Example 2 | 1C, 0.5 wt % | 36.5 |
| Example 3 | 2C, 0.5 wt % | 34.9 |
| Example 4 | 3C, 0.5 wt % | 20.0 |

Comparative Examples 3 and 4 and Examples 5 to 9

The procedure in Examples 1 to 4 was followed except the base oil used was GTL oil. The results are shown in Table 2.

TABLE 2

| | Additive, wt % | Oxidation Induction Time, Minutes |
|---|---|---|
| Comp. 3 | None | 4.2 |
| Comp. 4 | L57, 0.5 wt % | 42.5 |
| Example 5 | 1B, 0.5 wt % | None for 200 minutes or >200 minutes |
| Example 6 | 1C, 0.5 wt % | 152.5 |
| Example 7 | 2C, 0.5 wt % | 99.1 |
| Example 8 | 3C, 0.5 wt % | 48.5 |
| Example 9 | 3D, 0.5 wt % | 172 minutes |

Comparative Example 5 and Examples 10 to 13

In these examples, formulations were evaluated for deposit control using the TEOST test, ASTM D 6335. The base oil in these examples was 150N mineral oil. The results are shown in Table 3.

TABLE 3

| | Additive, wt % | Deposit, mg. |
|---|---|---|
| Comp. 5 | L57, 0.26 wt % | 109.7 |
| Example 10 | 1B, 0.26 wt % | 41.6 |
| Example 11 | 1C, 0.26 wt % | 49.6 |
| Example 12 | 2C, 0.26 wt % | 16.3 |
| Example 13 | 3C, 0.26 wt % | 51.0 |

Comparative Example 6 and Examples 14 to 17

In these examples, the formulations were evaluated for deposit control using the TEOST test. A fully formulated synthetic motor oil was used. The results of the TEOST test are also given in Table 4.

TABLE 4

| | Additive, wt % | Deposit, mg. |
|---|---|---|
| Comp. 6 | L57, 0.26 wt % | 109.3 |
| Example 14 | 1B, 0.26 wt % | 2.0 |
| Example 15 | 1C, 0.26 wt % | 0.1 |
| Example 16 | 2C, 0.26 wt % | 1.1 |
| Example 17 | 3C, 0.26 wt % | 3.3 |

Comparative Examples 7 and 8 and Example 18

In the following example, the procedure in Examples 1 to 4 was followed except the base oil used was GTL oil and the antioxidant used was an unsubstituted N,N'-diaryl-o-phenylenediamine. The results are shown in Table 5. Even at $\frac{1}{10}^{th}$ concentration the OIT of unsubstituted N,N'-diaryl-o-phenylenediamine is higher than the commercial antioxidant L57.

TABLE 5

| | Additive, wt % | Oxidation Induction Time, Minutes |
|---|---|---|
| Comp. 7 | None | 4.2 |
| Comp. 8 | L57, 0.5 wt % | 42.5 |
| Example 18 | 1E, 0.05 wt % | 54.0 |

In the following examples, Examples 19 to 26, N,N'-diaryl-o-phenylenediamine antioxidants according to the invention are synthesized utilizing different raw materials as well as different catalysts.

Example 19

Synthesis of N,N'-diaryl-o-phenylenediamine from 1,2-dichlorobenzene and 2,6-dimethylaniline in the Presence of Palladium acetate/tri-t-butylphosphine Catalyst In an argon glove box, 0.80 mmol palladium acetate, $Pd(OAc)_2$, and 2.2 mmol of solid tri-t-butylphosphine, $P^tBu_3$, were combined in 20 mL of toluene. The mixture was stirred until the $Pd(OAc)_2$ dissolved. Twenty-five (25) mmol of 1,2-dichlorobenzene was added to the mixture followed by 75 mmol of 2,6-dimethylaniline and 75 mmol of sodium tert-butoxide, $NaO^tBu$. The reaction mixture was heated to about 110° C. and maintained at about 110° C. for approximately 14 h. After approximately 14 h, the argon glove box was opened and the reaction mixture was quickly quenched with aqueous ammonium chloride (40 g $NH_4Cl$ in 80 ml $H_2O$). The toluene layer was separated from the aqueous layer and washed twice with 80 mL with deionized water. The toluene layer was dried over magnesium sulfate, $MgSO_4$, and filtered. The toluene layer was concentrated on a rotary evaporator until crystals began to form. The toluene layer with crystals was cooled to about −10° C. and maintained at this temperature for 24 hours. The crystals were isolated by filtration and dried under vacuum. The yield of isolated N,N'-diaryl-o-phenylenediamine was 5.11 grams, GC yield of 100%. The GC/MS spectrum suggests that the product is a single compound having a mass of m/e316.

Example 20

Synthesis of N,N'-diaryl-o-phenylenediamine from 1,2-dibromobenzene and 2,6-dimethylaniline in the Presence of Preformed Palladium Complex Coupling Catalyst In an argon glove box, 0.168 mmol dichlorobis(di-tert-butylphenylphosphine)palladium (II) was combined with 40 mL toluene and stirred for about 5 minutes. To the mixure, 8.5 mmol of 1,2-dibromobenzene was added followed by 25 mmol of 2,6-dimethylaniline and 25 mmol of sodium tert-butoxide, $NaO^tBu$. The reaction mixture was heated to about 110° C. and maintained at about 110° C. for approximately 14 h. After approximately 14 h, the argon glove box was opened and the reaction mixture was quickly quenched with aqueous ammonium chloride (10 g $NH_4Cl$ in 25 ml $H_2O$). The toluene layer was separated from the aqueous layer and washed twice with 80 mL is deionized water. The toluene layer was dried over magnesium sulfate, $MgSO_4$, and filtered. The toluene layer was concentrated on a rotary evaporator until crystals began to form. The toluene layer with crystals was cooled to about −10° C. and maintained at this temperature for 24 hours. The crystals were isolated by filtration and dried under vacuum. The yield of isolated N,N'-diaryl-o-phenylenediamine was 1.44 grams, GC yield of 100%. The GC/MS spectrum suggests that the product is a single compound having a mass of m/e316.

Example 21

Synthesis of N,N'-diaryl-o-phenylenediamine from 1,2-dichlorobenzene and 2,6-dimethylaniline in the Presence of Preformed Palladium Complex Coupling Catalyst In an argon glove box, 0.168 mmol dichlorobis(di-tert-butylphenylphosphine)palladium (II) was combined with 40 mL of toluene and stirred for about 5 minutes. To the mixture, 13.6 mmol of 1,2-dichlorobenzene was added followed by 25 mmol of 2,6-dimethylaniline and 25 mmol of sodium tert-butoxide, NaO$^t$Bu. The reaction mixture was heated to about 110° C. and maintained at about 110° C. for approximately 14 h. After approximately 14 h, the argon glove box was opened and the reaction mixture was quickly quenched with aqueous ammonium chloride (20 g NH$_4$Cl in 60 ml H$_2$O). The toluene layer was separated from the aqueous layer and washed twice with 80 mL deionized water. The toluene layer was dried over magnesium sulfate, MgSO$_4$, and filtered. The toluene layer was concentrated on a rotary evaporator until crystals began to form. The solution was cooled to about −10° C. and maintained at this temperature for 24 hours. The crystals were isolated by filtration and dried under vacuum. The yield of isolated N,N'-diaryl-o-phenylenediamine was 2.64 grams, GC yield of 100%. The GC/MS spectrum suggests that the product is a single compound having a mass of m/e316.

Example 22

Synthesis of N,N'-diaryl-o-phenylenediamine from 1,2-dibromobenzene and 2,6-dimethylaniline in the Presence of Preformed Palladium Complex Coupling Catalyst In an argon glove box, 0.084 mmol dichloro[1,1'-bis(di-tert-butylphosphino)ferrocene]palladium(II) was combined with 40 mL of toluene and stirred for 5 minutes. To the mixture, 8.5 mmol of 1,2-dibromobenzene was added followed by 25 mmol of 2,6-dimethylaniline and 25 mmol of sodium tert-butoxide, NaO$^t$Bu. The reaction mixture was stirred at 25° C. for 12 hours.

After running a small amount of product in a GC/MS, it was found that the product was a mixture of desirable product with me 316 and unreacted reagents suggesting that the reaction can be carried out at lower temperatures.

Example 23

Synthesis of N,N'-diaryl-o-phenylenediamine from 1,2-phenylenediamine and 2-choro-m-xylene in the Presence of Palladium acetate/tri-t-butylphosphine Catalyst In an argon glove box, 0.40 mmol palladium acetate, Pd(OAc)$_2$, and 1.1 mmol of solid tri-t-butylphosphine, PtBu$_3$, were combined in 40 mL of toluene and stirred until the Pd(OAc)$_2$ dissolved. To the mixture, 12.5 mmol of 1,2-phenylenediamine was added followed by 37.5 mmol of 2-chloro-1,3-dimethylbenzene and 37.5 mmol of sodium tert-butoxide, NaO$^t$Bu. The reaction mixture was heated to about 110° C. and maintained at about 110° C. for approximately 14 h. After approximately 14 h, the argon glove box was opened and the reaction mixture was quickly quenched with aqueous ammonium chloride (20 g NH$_4$Cl in 60 ml H$_2$O). The toluene layer was separated from the aqueous layer and washed twice with 50 mL deionized water. The toluene layer was dried over magnesium sulfate, MgSO$_4$, and filtered. The toluene layer was concentrated on a rotary evaporator until crystals began to form. The solution was cooled to about −10° C. and maintained at this temperature for 24 hours. The crystals were isolated by filtration and dried under vacuum. The yield of isolated N,N'-diaryl-o-phenylenediamine was 2.87 grams, GC yield of 100%. The GC/MS spectrum suggests that the product is a single compound having a mass of m/e316.

Example 24

Synthesis of N,N'-bis(2,6-dimethylphenyl)-4,5-dimethyl-o-phenylenediamine from 4,5-dibromo-o-xylene and 2,6-dimethylaniline in the Presence of Palladium acetate/tri-t-butylphosphine In an argon glove box, 0.27 mmol of palladium acetate, Pd(OAc)$_2$ and 0.73 mmol of solid tri-t-butylphosphine P$^t$Bu$_3$ were combined in 40 mL of toluene. The mixture was stirred until the Pd(OAc)$_2$ dissolved. 8.3 mmol of 4,5-dibromo-o-xylene was added to the mixture followed by 25 mmol of 2,6-dimethylaniline and 25 mmol of sodium tert-butoxide, NaO$^t$Bu. The reaction mixture was heated to about 110° C. and maintained at about 110° C. for approximately 14 h. After several hours, a precipitate formed. The precipate may not always be visible. The argon glove box was opened and the reaction mixture was quickly quenched with aqueous ammonium chloride (4 g NH$_4$Cl in 20 ml H$_2$O). The toluene layer was separated from the aqueous layer and washed twice with 80 mL with deionized water. The toluene layer was dried over magnesium sulfate, MgSO$_4$, and filtered. The toluene layer was concentrated on a rotary evaporator until crystals began to form. The toluene layer with crystals was cooled to about −10° C. and maintained at this temperature for 24 hours. The crystals were isolated by filtration and dried under vacuum. The yield of isolated N,N'-bis(2,6-dimethylphenyl)-4,5-dimethyl-o-phenylenediamine was 1.1 g, GC yield 100%. The GC/MS spectrum suggests that the product is a single compound and has mass of m/e 344.

Example 25

Synthesis of N,N'-Bis(2,4,6-trimethylphenyl)-o-phenylenediamine from 1,2-dibromobenzene and 2,4,6-trimethylaniline in the Presence of Palladium acetate/tri-t-butylphosphine In an argon glove box, 0.40 mmol of palladium acetate, Pd(OAc)$_2$ and 2.2 mmol of solid tri-t-butylphosphine P$^t$Bu$_3$ were combined in 40 mL of toluene. The mixture was stirred until the Pd(OAc)$_2$ dissolved. 12.5 mmol of 1,2-dibromobenzene was added to the mixture followed by 37.5 mmol of 2,4,6-trimethylaniline and 37.5 mmol of sodium tert-butoxide, NaO$^t$Bu. The reaction mixture was heated to about 110° C. and maintained at about 110° C. for approximately 14 h. After several hours, a precipitate formed. The precipate may not always be visible. The argon glove box was opened and the reaction mixture was quickly quenched with aqueous ammonium chloride (20 g NH$_4$Cl in 60 ml H$_2$O). The toluene layer was separated from the aqueous layer and washed twice with 80 mL with deionized water. The toluene layer was dried over magnesium sulfate, MgSO$_4$, and filtered. The toluene layer was concentrated on a rotary evaporator until crystals began to form. The toluene layer with crystals was cooled to about −10° C. and maintained at this temperature for 24 hours. The crystals were isolated by filtration and dried under vacuum. The yield of isolated N,N'-Bis(2,4,6-trimethylphenyl)-o-phenylenediamine was 1.96 g, GC yield 100%. The GC/MS spectrum suggests that the product is a single compound and has mass of m/e 344.

Example 26

Synthesis of Unsubtituted N,N'-bisphenyl-o-phenylenediamine from 1,2-dibromobenzene and aniline in the Presence of Palladium acetate/tri-t-butylphosphine In an argon glove box, 0.4 mmol of palladium acetate, Pd(OAc)$_2$ and 1.1 mmol of solid tri-t-butylphosphine P$^t$Bu$_3$ were combined in 20 mL of toluene. The mixture was stirred until the Pd(OAc)$_2$ dissolved. 12.7 mmol of 1,2-dibromobenzene was added to the mixture followed by 37.6 mmol of aniline and 37.5 mmol of sodium tert-butoxide, NaO$^t$Bu. The reaction mixture was heated to about 110° C. and maintained at about 110° C. for approximately 14 h. After several hours, a precipitate formed. The precipate may not always be visible. The argon glove box was opened and the reaction mixture was quickly quenched with aqueous ammonium chloride (20 g NH$_4$Cl in 80 ml H$_2$O). The toluene layer was separated from the aqueous layer and washed twice with 80 mL with deionized water. The toluene layer was dried over magnesium sulfate, MgSO$_4$, and filtered. The toluene layer was concentrated on a rotary evaporator until crystals began to form. The toluene layer with crystals was cooled to about −10° C. and maintained at this temperature for 24 hours. The crystals were isolated by filtration and dried under vacuum. The yield of isolated unsubstituted N,N'-bisphenyl-o-phenylenediamine was 1.4 g, GC yield 100%. The GC/MS spectrum suggests that the product is a single compound and has mass of m/e 260.

It will thus be seen that the objects set forth above, among those apparent in the preceding description, are efficiently attained and, since certain changes may be made in carrying out the present invention without departing from the spirit and scope of the invention, it is intended that all matter contained in the above description and shown in the accompanying drawing be interpreted as illustrative and not in a limiting sense.

It is also understood that the following claims are intended to cover all of the generic and specific features of the invention herein described and all statements of the scope of the invention, which as a matter of language, might be said to fall therebetween.

What is claimed is:

1. A composition comprising a major amount of a lubricant or hydraulic fluid and an effective amount of at least one N, N'-diaryl-o-phenylenediamine antioxidant represented by Formula I,

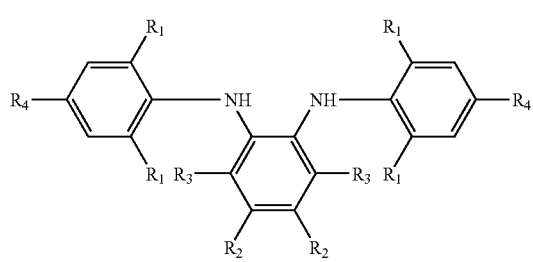

where R$_1$ is H or C$_1$ to C$_{12}$ alkyl, R$_2$ is H or C$_1$ to C$_{12}$ alkyl, and R$_3$ and R$_4$ are independently H or C$_1$ to C$_{12}$ alkyl.

2. The composition of claim 1, wherein R$_1$ is C$_1$ to C$_{10}$ alkyl, R$_2$ and R$_3$ independently are H or C$_1$ to C$_2$ alkyl, and R$_4$ is H or C$_1$ to C$_4$ alkyl.

3. The composition of claim 1, wherein R$_1$ is C$_1$ alkyl, and R$_2$, R$_3$ and R$_4$ are H.

4. The composition of claim 1, wherein the antioxidant is 1,2-benzenediamine, N,N'-bis(2,6-dimethylphenyl), 1,2-benzenediamine, N, N'-bis [2, 6-bis (1-methyl ethyl) phenyl] or 1, 2-benzenediamine, N, N'-bis [2, 6-bis (1-methyl ethyl) phenyl]-4, 5 dimethyl.

5. The composition of claim 1, wherein the antioxidant is 1,2-benzenediamine, N,N'-bis(2,6-dimethylphenyl).

6. The composition of claim 1, wherein the antioxidant is present in the range of about 0.001 wt % to about 5 wt % based on the total weight of the composition.

7. The composition of claim 1 wherein the composition comprises a natural oil or a synthetic oil.

8. The composition of claim 7 wherein synthetic oil is derived from a Fischer-Tropsch wax.

9. The composition of claim 1 including at least one additional lubricating oil additive or hydraulic fluid additive.

10. A method of improving antioxidative properties of a lubricant or hydraulic fluid composition comprising adding an effective amount of at least one N, N'-diaryl-o-phenylenediamine antioxidant according to claim 1 to said composition.

11. The method of claim 10, wherein the antioxidant is present in an amount ranging from about 0.001 wt % to about 5 wt %, based on the total weight of the composition.

12. The method of claim 10, wherein the antioxidant is represented by Formula 1

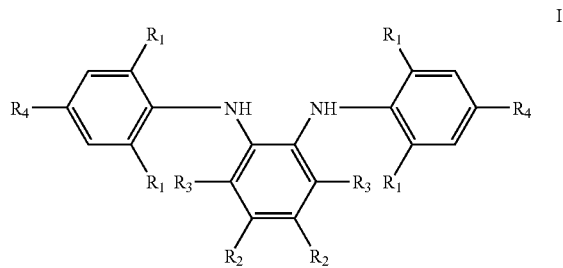

where R$_1$ is C$_1$ to C$_{12}$ alkyl, R$_2$ is H or C$_1$ to C$_{12}$ alkyl, R$_3$ and R$_4$ are independently H or C$_1$ to C$_{12}$ alkyl; and, further comprising at least one additional lubricating oil additive or hydraulic fluid additive.

* * * * *